US00PP36414P2

(12) United States Plant Patent
Hartman

(10) Patent No.: US PP36,414 P2
(45) Date of Patent: Jan. 28, 2025

(54) ***CALADIUM* PLANT NAMED 'CST OF14-255'**

(50) Latin Name: ***Caladium* X *hortulanum***
Varietal Denomination: CST OF14-255

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,749

(22) Filed: May 7, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ..... A01H 5/12; A01H 5/00; A01H 6/10
See application file for complete search history.

(56) References Cited

U.S. PATENT DOCUMENTS

PP31,599 P2 * 3/2020 Hartman ..... A01H 5/12
Plt./373

* cited by examiner

*Primary Examiner* — June Hwu
(74) *Attorney, Agent, or Firm* — C. Anne Whealy

(57) ABSTRACT

A new and distinct cultivar of *Caladium* plant named 'CST OF14-255', characterized by its upright plant habit and intermediate in height; dense, leafy and bushy appearance; vigorous growth habit and rapid growth rate; fancy-type leaves that are white to greenish white in color with random and numerous dark red-colored spots and flecks with dark green-colored margins and venation; and petioles that are green to tannish green in color with brown-colored stippling and streaks.

4 Drawing Sheets

Figure 1:
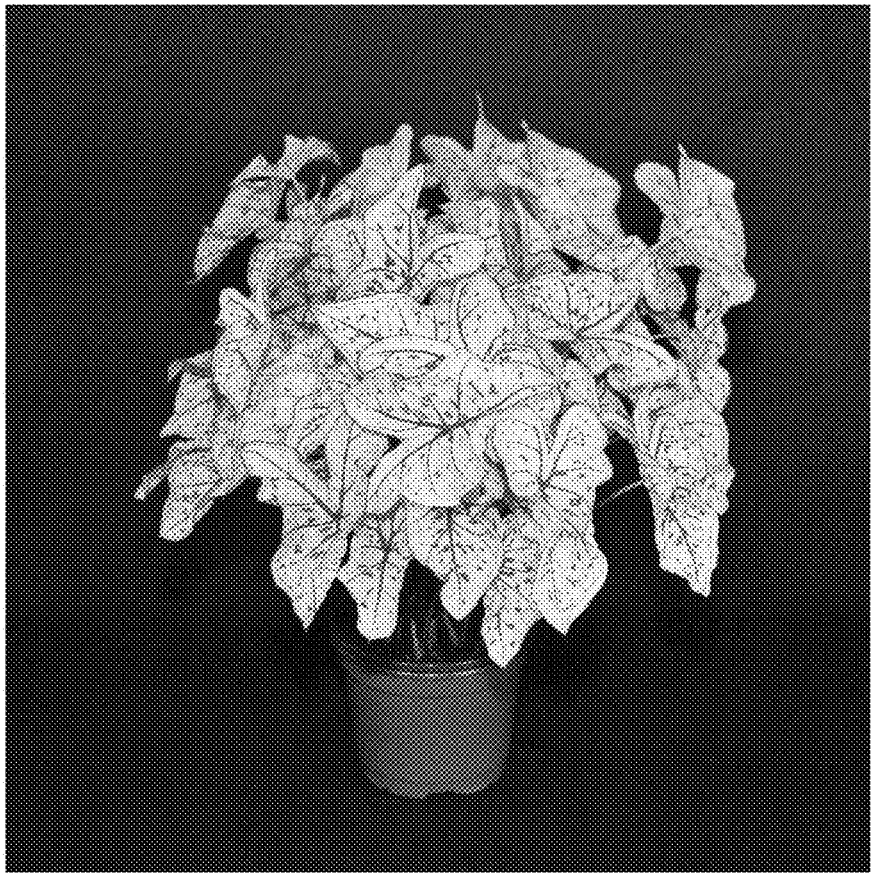

Botanical designation: *Caladium* X *hortulanum*.
Cultivar denomination: 'CST OF14-255'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'CST OF14-255'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April 2013 in Avon Park, Florida of *Caladium* X *hortulanum* 'White Cap', disclosed in U.S. Plant Pat. No. 23,815, as the female, or seed, parent with *Caladium* X *hortulanum* 'Gingerland', not patented, as the male, or pollen, parent. The new *Caladium* plant was discovered and selected by the Inventor as a single plant within the progeny of the stated cross-pollination in a controlled outdoor nursery environment in Avon Park, Florida in September 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'CST OF14-255'. These characteristics in combination distinguish 'CST OF14-255' as a new and distinct *Caladium* plant:

1. Upright plant habit and intermediate in height; dense, leafy and bushy appearance.
2. Vigorous growth habit and rapid growth rate.
3. Fancy-type leaves that are white to greenish white in color with random and numerous dark red-colored spots and flecks with dark green-colored margins and venation.
4. Petioles that are green to tannish green in color with brown-colored stippling and streaks.

Plants of the new *Caladium* differ primarily from plants of the female parent, 'White Cap', in leaf color as leaves of plants of the new *Caladium* are white to greenish white in color with random and numerous dark red-colored spots and flecks with dark green-colored margins and venation whereas leaves of plants of 'White Cap' have white, greyed green and green speckled interveinal areas, dark green-colored margins and white-colored venation. In addition, petioles of plants of the new *Caladium* are green to tannish green in color with brown-colored stippling and streaks whereas petioles of plants of 'White Cap' are green tinged with brown in color.

Plants of the new *Caladium* differ primarily from plants of the male parent, 'Gingerland', in the following characteristics:

1. Plants of the new *Caladium* grow more rapidly than plants of 'Gingerland'.
2. Leaves of plants of the new *Caladium* are white to greenish white in color with random and numerous dark red-colored spots and flecks with dark green-colored margins and venation whereas leaves of plants of 'Gingerland' are green in color with white-colored interveinal areas, white and pink-colored venation, dark red-colored spots and green-colored margins.
3. Petioles of plants of the new *Caladium* are green to tannish green in color with brown-colored stippling and streaks whereas petioles of plants of 'Gingerland' are tannish pink to tannish green in color with darker green-colored stippling, streaks and tessellations.

Plants of the new *Caladium* can be compared to plants of *Caladium* X *hortulanum* 'Splash of Wine', disclosed in U.S. Plant Pat. No. 31,599. In side-by-side comparisons, plants of the new *Caladium* differ primarily from plants of 'Splash of Wine' in the following characteristics:

1. Plants of the new *Caladium* are taller than plants of 'Splash of Wine'.
2. Leaves of plants of the new *Caladium* are white to greenish white in color with random and numerous dark red-colored spots and flecks with dark green-colored margins and venation whereas leaves of plants of 'Splash of Wine' have dark green-colored venation with interveinal areas that are greenish white or white flushed with red and light red in color and densely covered with red purple-colored spots and narrow dark green-colored margins.
3. Petioles of plants of the new *Caladium* are green to tannish green in color with brown-colored stippling and streaks whereas petioles of plants of 'Splash of Wine' are tannish pink in color with brownish green-colored stripes and streaks.

Plants of the new *Caladium* can also be compared to plants of *Caladium* X *hortulanum* 'Heart and Soul', disclosed in U.S. Plant Pat. No. 31,567. In side-by-side comparisons, plants of the new *Caladium* differ primarily from plants of 'Heart and Soul' in leaf color as leaves of plants of the new *Caladium* are white to greenish white in color with random and numerous dark red-colored spots and flecks with dark green-colored margins and venation whereas leaves of plants of 'Heart and Soul' are dark green in color with greyed purple-colored venation, white, green, red and greyed purple-colored interveinal areas, and dark red-colored random spots. In addition, petioles of plants of the new *Caladium* are green to tannish green in color with brown-colored stippling and streaks whereas petioles of plants of 'Heart and Soul' are tannish pink in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'CST OF14-255' grown in a container that has had its tuber de-eyed prior to planting.

Figure 2:
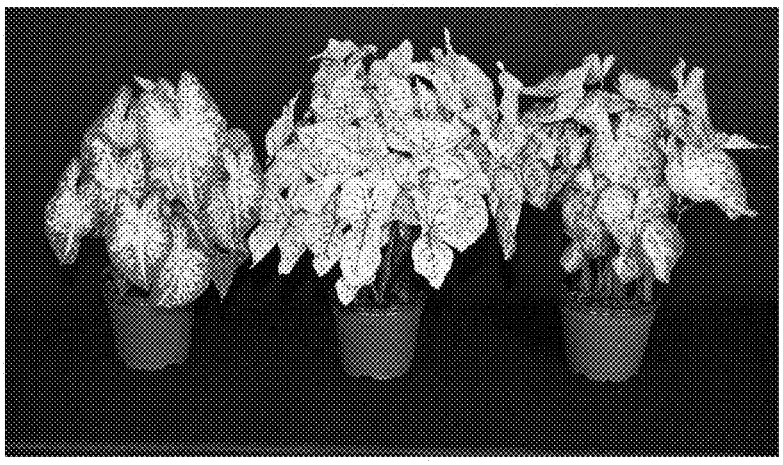

The photograph at the top of the second sheet (FIG. 2) is side perspective view of typical plants of the female parent, 'White Cap' (left), 'CST OF14-255' (center) and the male parent, 'Gingerland' (right).

Figure 3:
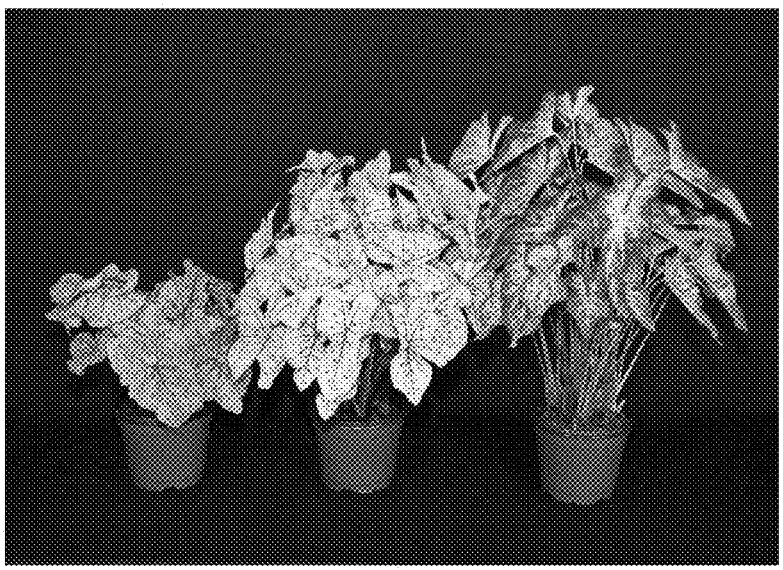

The photograph at the bottom of the second sheet (FIG. 3) is side perspective view of typical plants of 'Splash of Wine' (left), 'CST OF14-255' (center) and 'Heart and Soul' (right).

Figure 4:
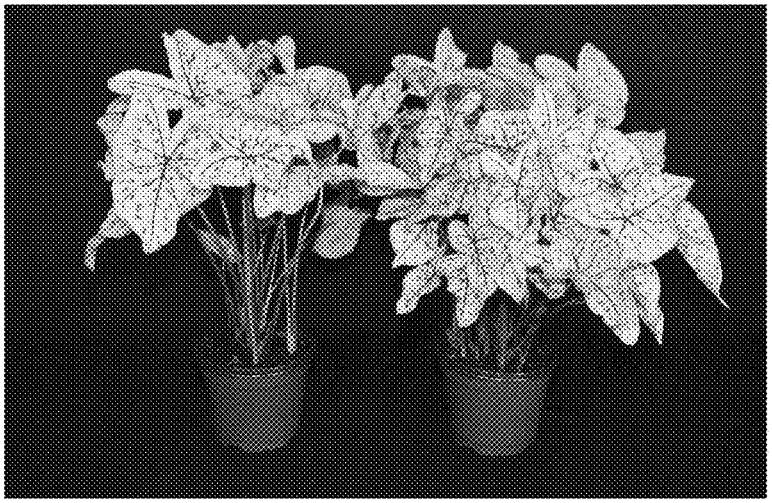

The photograph at the top of the third sheet (FIG. 4) is a comparison view of typical plants of 'CST OF14-255' grown in containers, the plant on the left has not had its tuber de-eyed and the plant on the right has had its tuber de-eyed prior to planting.

Figure 5:
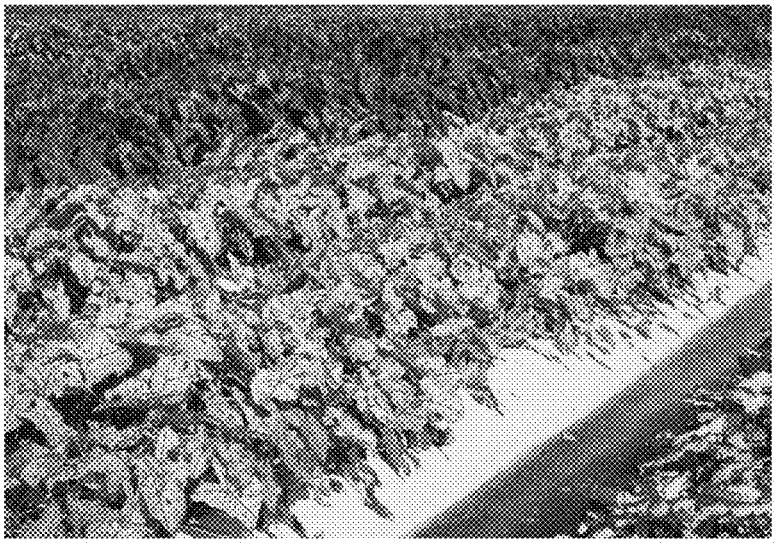

The photograph at the bottom of the third sheet (FIG. 5) is a side perspective view of typical plants of 'CST OF14-255' grown in an open production field.

Figure 6:
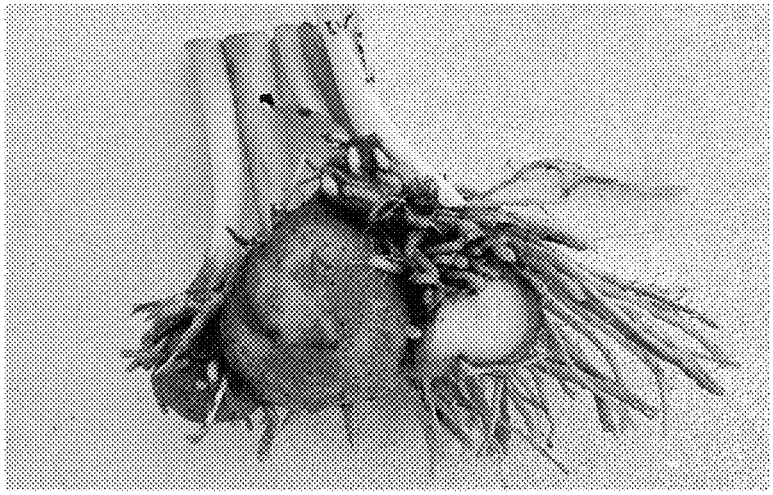

The photograph at the top of the fourth sheet (FIG. 6) is a close-up view of typical freshly-harvested tubers with roots and leaf petioles of 'CST OF14-255'.

Figure 7:
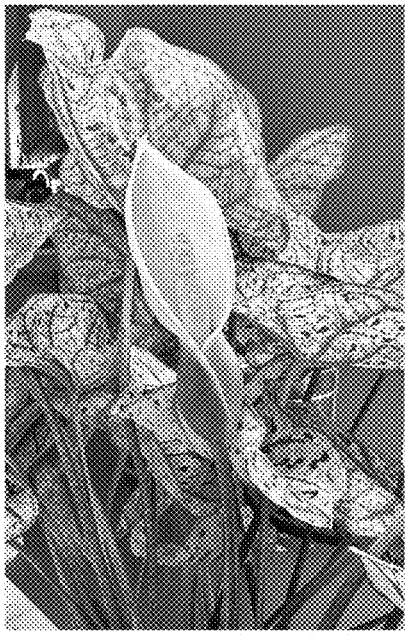

The photograph at the bottom of the fourth sheet (FIG. 7) is a close-up view of a typical flowering plant of 'CST OF14-255'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were twelve weeks old and plants grown in the outdoor nursery were six months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'CST OF14-255'.

Parentage:

*Female, or seed, parent.*—*Caladium* X *hortulanum* 'White Cap', disclosed in U.S. Plant Pat. No. 23,815.

*Male, or pollen, parent.*—*Caladium* X *hortulanum* 'Gingerland', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and branched; individual segments are elliptic or irregular in shape. Height: About 2.9 cm to 3 cm. Diameter: About 3.9 cm to 7.2 cm. Segment height: About 2.5 cm to 2.6 cm. Segment diameter: About 2 cm to 2.6 cm. Axillary bud shape: Roughly triangular. Axillary bud height: About 2.5 mm. Axillary bud width: About 2 mm. Texture: Thick, starchy; somewhat brittle. Color: Periderm, freshly-harvested: Close to N199C. Periderm, dried: Close to 200A. Epidermis: Close to 158B. Cortical tissue: Close to 155D. Axillary buds: Close to 36D. Root description: Relatively thin, fleshy contractile roots with a moderate number of thin lateral branches; color, close to N155D; actual color of the roots is dependent on substrate composition, water quality, fertilizer type and formulation, substrate temperature and physiological age of roots; root density, dense.

Plant description:

*Plant type*.—Herbaceous perennial; suitable as a potted plant in containers 10-cm to 25-cm and suitable as a landscape plant in shaded areas.

*Plant and growth habit*.—Upright plant habit; intermediate in height; dense, leafy and bushy appearance; vigorous growth habit and rapid growth rate; potted plants finish in saleable form in about six to seven weeks after planting tubers; leaf petioles and leaves arise from one or more growing points on tubers; leaf petioles initially upright and leaning outwardly with development.

*Plant height, from soil level to top of foliar plane, shade house-grown potted plants*.—About 30 cm to 34 cm.

*Plant height, from soil level to top of floral plane, shade house-grown potted plants*.—About 24.8 cm.

*Plant diameter, shade house-grown potted plants*.—About 35 cm to 38 cm.

*Number of shoots per plant, shade house-grown potted plants, tubers de-eyed*.—About five to seven develop per #1 tuber.

*Number of shoots per plant, shade house-grown potted plants, tubers not de-eyed*.—About three to four develop per #1 tuber.

*Cataphylls, shade house-grown potted plants*.—Length: About 3 cm to 5.5 cm. Width: About 1.5 cm. Shape: Lanceolate. Apex: Acute to acuminate. Base: Sheathing the stem. Texture, outer and inner surfaces: Smooth, glabrous. Color, outer surface: Close to 147C and 147D, streaked and stippled with close to 147A and tinged with close to 200A; color becoming closer to 200A and 200B with subsequent development. Color, inner surface: Close to 155C; colors and color patterns may be visible from outer surface visible.

Leaf description:

*Arrangement and type*.—Alternate; simple; fancy-type.

*Length, shade house-grown potted plants*.—About 13 cm to 15.5 cm.

*Width, shade house-grown potted plants*.—About 8 cm to 9.5 cm; when flattened, about 9.4 cm to 10.5 cm.

*Shape*.—Ovate with cordate tendencies.

*Apex*.—Acute to acuminate.

*Base*.—Sagittate to peltate, cordate.

*Margin*.—Entire; wavy with broad undulations.

*Texture and luster, upper surface*.—Rugose, glabrous; rigid; dull sheen.

*Texture and luster, lower surface*.—Rugose, glabrous; slightly glaucous; dull sheen.

*Venation pattern*.—Pinnate and palmate.

*Color, shade house-grown potted plants*.—When developing and fully expanded leaves, upper surface: Ground color: Close to 155A and/or 155C. Margins: Close to 147A; edges, close to 187A. Basal notch: Close to 187C. Midvein and primary venation: Close to 147A tinged with close to 137A. Secondary venation: Close to 147A to 147B. Random spots: Close to 185A. When developing and fully expanded leaves, lower surface: Ground color: Close to 155C, 155D and/or 138B. Margins: Close to 191A and close to 191A tinged with close to 137D; edges, close to 187B. Basal notch: Close to 187D. Leaf/petiole junction: Close to N186C. Midvein: Close to 194B to 194C, distally tinged with close to 183D. Lateral venation: Close to 137D. Random spots: Close to 187C.

*Petioles*.—Aspect: Initially upright and straight and leaning outwardly with development; flexible. Length, shade house-grown potted plants: About 25.5 cm to 35.5 cm. Diameter, distally, shade house-grown potted plants: About 2.5 mm to 3 mm. Diameter, proximally, shade house-grown potted plants: About 3.5 mm to 5 mm. Texture: Smooth, glabrous; slightly glaucous. Color, shade house-grown potted plants: Close to 147C to 147D, 156C and N170D with stippling and streaks, close to 200A and tinged with close to 147A; just below the leaf junction, close to 147C, 147D, 196C variably stippled and streaked with close to 200D. Wing length, shade house-grown potted plants: About 3.5 cm to 4.8 cm. Wing diameter, shade house-grown potted plants: About 8 mm. Texture and luster, inner and outer surfaces: Smooth, glabrous; dull to slightly glossy. Wing color, shade house-grown potted plants: Outer surface: Close to 147C and 147D stippled and streaked with close to 147A and tinged with close to 200A. Inner surface: Close to 155C; colors and patterns from the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about eight weeks after growth commences; inflorescences last about three days before fading; inflorescences persistent.

*Spathe*.—Length, overall: About 9 cm. Length, distal open portion: About 5.7 cm. Length, proximal closed portion: About 3.3 cm. Width, distal open portion: About 2.7 cm. Depth, distal open portion: About 2.2 cm. Width, at constriction: About 9 mm to 12 mm. Width, proximal closed portion: About 1.7 cm to 1.9 cm. Shape, open portion: Elliptic to slightly obovate. Apex: Acute. Base: Acute. Margin: Entire; slightly reflexed. Texture and luster, front surface: Smooth, glabrous; dull sheen. Texture and luster, rear surface: Smooth, glabrous; distal open portion, dull sheen; proximal closed portion, slightly glaucous. Color, front surface: Distal open portion: Close to 155B; with subsequent development, distally becoming closer to 199B. Proximal closed portion: Close to 147D, towards the base, tinged with close to 187A to 187B; color does not change with subsequent development. Color, rear surface: Distal open portion: Close to 155B to 155C; central area, flushed with close to 150D; color does not change with subsequent development. Proximal closed portion: Close to 147C to 147D; color does not change with subsequent development.

*Spadix*.—Length, overall: About 5.7 cm. Length, male flower zone: About 4.5 cm. Length, sterile zone: About 1.4 cm. Length, female flower zone: About 1.2 cm. Diameter, male flower zone: About 8 mm. Diameter, sterile flower zone: About 6 mm. Diameter, female flower zone: About 9 mm. Shape: Columnar, spindle-shaped. Apex: Acute to obtuse, rounded. Base: Obtuse. Aspect: Upright. Color, mature, male zone: Close to 158D. Color, mature, sterile zone: Close to 158D. Color, mature, female zone: Close to 158A. Male flowers: Quantity per spadix: About 75. Shape: Obovate. Height: About 2 mm. Diameter: About 1.5 mm to 2 mm. Pollen amount: Moderate. Pollen color: Close to 11C. Female flowers: Quantity per spadix: About 185. Shape: Obovate. Height: About 1.5 mm to 2 mm. Diameter: About 1 mm to 1.2 mm. Stigma color: Close to 158A. Ovary color: Close to 158A.

*Scapes*.—Length: About 19.1 cm. Diameter: About 4 mm. Strength: Sturdy; flexible. Aspect: Mostly erect, straight. Texture and luster: Smooth, glabrous; slightly glossy and distally, glaucous. Color: Close to 199D tinged with close to 147D and stippled and streaked with close to 200A and 200C; occasionally with stripes, close to 199C and 199D; just below spathe, close to 147C and 147D faintly stippled and streaked with close to 200C.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'CST OF14-255' as herein illustrated and described herein.

* * * * *